United States Patent
Abduljauwad et al.

(10) Patent No.: US 11,771,716 B2
(45) Date of Patent: Oct. 3, 2023

(54) NANOCLAYS FOR THE CONTROL OF MELANOMA CELL PROLIFERATION AND CELL VIABILITY

(71) Applicant: King Fahd University of Petroleum and Minerals, Dhahran (SA)

(72) Inventors: Sahel N. Abduljauwad, Dhahran (SA); Habib-ur-Rehman Ahmed, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 16/439,126

(22) Filed: Jun. 12, 2019

(65) Prior Publication Data

US 2020/0390804 A1 Dec. 17, 2020

(51) Int. Cl.
*A61K 33/06* (2006.01)
*A61K 31/404* (2006.01)
*A61K 9/00* (2006.01)
*A61K 45/06* (2006.01)

(52) U.S. Cl.
CPC ............ *A61K 33/06* (2013.01); *A61K 9/0014* (2013.01); *A61K 9/0019* (2013.01); *A61K 31/404* (2013.01); *A61K 45/06* (2013.01)

(58) Field of Classification Search
CPC combination set(s) only.
See application file for complete search history.

(56) References Cited

U.S. PATENT DOCUMENTS 8,563,595 B2 * 10/2013 Chianelli ............... A61K 33/06
 514/418
2013/0101643 A1 4/2013 Scruggs

FOREIGN PATENT DOCUMENTS

| CN | 100490908 C | 5/2009 |
| CN | 107473269 A | 12/2017 |
| CN | 105381462 B | 4/2018 |
| WO | 2013/016999 A1 | 2/2013 |

OTHER PUBLICATIONS

Pandolfino (Comparison of three culture media for the establishment of melanoma cell lines, Cytotechnology (2010) 62:403-412).*
Genzel (Amino acid analysis in mammalian cell culture media containing serum and high glucose concentrations by anion exchange chromatography and integrated pulsed amperometric detection, Analytical Biochemistry 335 (2004) 119-125).*
Gaharwar (2D Nanoclay for Biomedical Applications: Regenerative Medicine, Therapeutic Delivery, and Additive Manufacturing, Adv. Mater, Apr. 3, 2019, 31, pp. 1-28).*
Cervini-Silva, et al.; Anti-inflammatory, anti-bacterial, and cytotoxic activity of fibrous clays ; Colloids and Surfaces B: Biointerfaces, vol. 129 ; pp. 1-6 ; May 1, 2015 ; Abstract Only ; 2 Pages.
Kouser, et al. ; Na-Montmorillonite-Dispersed Sustainable Polymer Nanocomposite Hydrogel Films for Anticancer Drug Delivery ; ACS Omega 3 ; pp. 15809-15820 ; 2018 ; 12 Pages.
Dong, et al. ; Poly(D,L-lactide-co-glycolide)/montmorillonite nanoparticles for oral delivery of anticancer drugs ; Biomaterials, vol. 26, Issue 30 ; pp. 6068-6076 ; Oct. 2005 ; Abstract Only ; 2 Pages.

* cited by examiner

*Primary Examiner* — Kathrien A Hartsfield
(74) *Attorney, Agent, or Firm* — Oblon, McClelland, Maier & Neustadt, L.L.P.

(57) ABSTRACT

The invention pertains to a method for reducing proliferation or viability of melanoma cells by contacting the cells with nanoclay. It also involves pharmaceutical composition containing nanoclay for treatment of melanoma.

18 Claims, 4 Drawing Sheets

NANOCLAYS FOR THE CONTROL OF MELANOMA CELL PROLIFERATION AND CELL VIABILITY

BACKGROUND OF THE INVENTION

Field of the Invention

The invention pertains to skin cancer treatments using nanoclays and to therapeutic and prophylactic nanoclay compositions.

Description of Related Art

Non-cancerous cells must pass a series of checkpoints that regulate cell proliferation and migration; Baba, A. I., & Câtoi, C. (2007). Tumor cell morphology. These checkpoints are regulated by several intracellular and extracellular signals. When precancerous or cancerous cells bypass these checkpoints increased cellular proliferation and, eventually, metastasis to vital organs such as the liver, brain, and lungs; can occur Gruber, F., Kaštelan, M., Brajac, I., Saftić, M., Peharda, V., Čabrijan, L. & Simonić, E. (2008). Molecular and genetic mechanisms in melanoma. Collegium antropologicum, 32(2), 147-152.

Unlike many forms of cancer, the incidence of melanoma has increased over the last two decades; Hsiao, W. W., & Liu, L. (2010). The role of traditional Chinese herbal medicines in cancer therapy—from TCM theory to mechanistic insights. Planta Medica, 76(11), 1118-1131. Current conventional therapies for melanoma include excisional surgery, immune therapy, and targeted therapy; Grob, J. J., Amonkar, M. M., Karaszewska, B., Schachter, J., Dummer, R., Mackiewicz, A. & Rutkowski, P. (2015). Comparison of dabrafenib and trametinib combination therapy with vemurafenib monotherapy on health-related quality of life in patients with unresectable or metastatic cutaneous BRAF Va1600-mutation-positive melanoma (COMBI-v): results of a phase 3, open-label, randomized trial. *The Lancet Oncology*, 16(13), 1389-1398; da Rocha Dias, S., Salmonson, T., van Zwieten-Boot, B., Jonsson, B., Marchetti, S., Schellens, J. H.,& Pignatti, F. (2013). The European Medicines Agency review of vemurafenib (Zelboraf®) for the treatment of adult patients with BRAF V600 mutation-positive unresectable or metastatic melanoma: summary of the scientific assessment of the Committee for Medicinal Products for Human Use. *European journal of cancer*, 49(7), 1654-1661. However, there are many challenges associated with these melanoma treatments including selection of an efficacious treatment based on tumor size and location, resistance of melanoma cells to drug and other treatments, avoidance of adverse side effects, and efficacy of a treatment in a particular individual.

Nanoclays are nanosized natural materials originating from minerals of sedimentary rock and typically possess an aluminosilicate formula, $(Ca, Na, H)(Al, Mg, Fe, Zn)_2(Si, Al)_4O_{10}(OH)_2$-x $H_2O$; Zhang, Y., Long, M., Huang, P., Yang, H., Chang, S., Hu, Y., Mao, L. (2017). Intercalated 2D nanoclay for emerging drug delivery in cancer therapy. Nano Research, 10(8), 2633-2643. Their biomedical properties include high absorption, ability to engulf microbes, and low toxicity.

The most studied biomedical application of nanoclays includes carriers and complexes for anti-cancer drugs such as 5-fluorouracil and Trastuzumab; see Zhang, Y., et al., (2017). Intercalated 2D nanoclay for emerging drug delivery in cancer therapy. Nano Research, 10(8), 2633-2643; Chianelli, R. R., & Das, S. (2013). U.S. Pat. No. 8,563,595. Washington, D.C.: U.S. Patent and Trademark Office; Han, S., et al., (2014). Targeting of fluorescent palygorskite polyethyleneimine nanocomposite to cancer cells. Applied Clay Science, 101, 567-573; Sun, B., et al., Multifunctional poly (D, L-lactide-coglycolide)/montmorillonite (PLGA/MMT) nanoparticles decorated by Trastuzumab for targeted chemotherapy of breast cancer. Biomaterials, 29(4), 475-486; Lin, F. H., et al., (2002). A study of purified montmorillonite intercalated with 5-fluorouracil as drug carrier. Biomaterials, 23(9), 1981-1987; Bothiraja, C., et al., (2014). Chitosan coated layered clay montmorillonite nanocomposites modulate oral delivery of paclitaxel in colonic cancer. Materials Technology, 29(sup3), B120-B126; Kevadiya, B. D., et al., (2012). Montmorillonite/poly-(ε-caprolactone) composites as versatile layered material: reservoirs for anticancer drug and controlled release property. European Journal of Pharmaceutical Sciences, 47(1), 265-272.

Nanoclays have been proposed for treatment of proctitis, US 2013/0101643A1; as carriers for drugs, WO 2013/016999A, CN107473269A, Kouser et al., ACS Omega 3:15809 (2018), Dong, et al., Biomaterials 26:6068 (2005); for photothermal treatment in combination with gold nanoparticles, CN105381462B; and as ingredients in anti-infective medical polymers, CN100490908C.

Past work with fibrous clay sepiolites for cancer treatment has been variable and required high concentrations of fibrous clays, Cervini-Silva, et al., Colloids and Surfaces B 129:1-6 (2015). Conventional modes of treatment for melanoma have limited efficacy due to resistance, non-mutually exclusive mutations, and adverse side effects. For example, high concentrations of clay such as >300 µg/ml can lack selective toxicity against cancer cells and suffocate or kill normal as well as cancer cells.

In view of the above, the inventors sought to determine whether pharmaceutical compositions containing particular types of clay, such as palygorskite and/or montmorillonite, could reduce melanoma cell viability and proliferation and be useful, nontoxic treatments for skin cancer and for reducing the viability of melanoma cells in particular.

BRIEF SUMMARY OF THE INVENTION

Among its other aspects, the invention is directed to a method for reducing the viability and inhibiting proliferation of skin cancer cells using palygorskite and/or montmorillonite clays and to therapeutic and prophylactic compositions containing these clays. Other non-limiting embodiments of the invention include the following.

In one embodiment the invention is directed to a method for reducing melanoma cell growth viability that includes mixing the melanoma cells with a treatment composition consisting essentially of at least one nanoclay selected from the group consisting of at least one of a palygorskite and a montmorillonite as an active ingredient, to form a cell growth mixture, then incubating the cell growth mixture; wherein during the mixing the melanoma cells are present in a growth medium, wherein the treatment composition contains the active ingredient in an amount of from 1 to 25 µg/ml, and after the incubating the melanoma cell growth viability is reduced by at least 50% in comparison to the melanoma cell growth viability of a control growth mixture that is mixed with a control composition that is the same as the treatment composition but does not contain the active ingredient.

In one embodiment the invention is directed to a method for treating a subject having melanoma or another skin cancer comprising, consisting essentially of, or consisting of administering a composition, consisting essentially of, or consisting of at least one nanoclay selected from the group consisting of at least one of a palygorskite and a montmorillonite to the subject. This method may involve administering a composition containing a concentration ranging from 0.01, 0.02, 0.05, 0.1, 0.2, 0.5, 1, 2, 5, 10, 20, 50, 100, 120, 150, 200, 220, 250, 300, 400, 500, 600, 700, 800, 900, 1,000 or >1,000 μg of the at least one nanoclay per cc or per gram of the composition to skin cancer or melanoma cells. Preferably, a concentration of about 1 to 200 μg of the at least one nanoclay per cc or per gram of the total composition or about 2 to 20 of the at least one nanoclay per cc or per gram of the composition is administered. The at least one nanoclay used in the methods disclosed herein may comprise, consist essentially of, or consist of palygorskite, such as pFI-1: palygorskite which has the formula $(Mg, Al)_2Si_4O_{10}(OH) \cdot 4H_2O$.

In another embodiment, the at least one nanoclay may comprise, consist essentially of, or consist of a montmorillonite, such as SWy-3 which is a Na-rich montmorillonite having the formula $(Na, Ca)_{0.33}(Al, Mg)_2(Si_4O_{10})$.

In other embodiments, the at least one nanoclay used in the method may comprise, consist essentially of, or consist of a mixture of a palygorskite and a montmorillonite, such as those having the formula $(Mg, Al)_2Si_4O_{10}(OH) \cdot 4H_2O$ or a montmorillonite having the formula $(Na, Ca)_{0.33}(Al, Mg)_2(Si_4O_{10})$, such as a Na rich montmorillonite.

In one embodiment, the at least one nanoclay as disclosed herein is administered topically, orally, intradermally, subcutaneously, intravenously, intramuscularly, or otherwise parenterally, into or onto a melanoma lesion or melanoma or other skin cancer cells in the skin.

In some embodiments, the at least one nanoclay as disclosed herein is administered into or around a dermal site after removal of melanoma cells. For example, the nanoclay or a composition containing it may be applied to a surgical wound after removal of a melanoma lesion as a post-surgery treatment or prophylaxis.

In some embodiments, the at least one nanoclay as disclosed herein is administered to a subject who has had at least one other anti-cancer therapy, such as surgical excision of skin cancer cells, treatment with an anticancer drug or treatment with an immune system activator such as with at least one of nivolumab (Opdivo®), ipilimumab (Yervoy®).

Another aspect of the invention is directed to a composition comprising, consisting essentially of, or consisting of at least one nanoclay selected from the group consisting of palygorskite and montmorillonite and at least one oil, grease, alcohol, wax, surfactant, UV protectant, vitamin, amino acid, antibiotic, gel, propellant, polymer, or solid support. In some embodiments this composition is the form of an emulsion, lotion, paste, glue, salve, ointment, sunscreen, cosmetic, gel, liquid bandage, or foam. In other embodiments, the composition comprises at least one UV protectant, which may be a UVA or UVB protectant, such as a protectant selected from the group consisting of p-aminobenzoic acid, padimate O, phenylbenzimidazole sulfonic acid, cinoxate, dioxybenzone, oxybenzone, homosalate, menthyl anthranilate, octocrylene, octyl methoxycinnamate, octyl salicylate, sulisobenzone, trolamine salicylate, avobenzone, ecamsule, titanium dioxide, zinc oxide, amiloxate, benzophenone-9, 4-methylbenzylidene camphor, Mexoryl XL™ (terephthalylidene dicamphor sulfonic acid), neo Heliopan AP™ (bisdisulizole disodium), Parsol Max™ (methylene bis-benzotriazolyl tetramethylbutylphenol), Parsol Shield™ (bis-ethylhexyloxyphenol methoxyphenyl triazine), Parsol SLX™ (polysilicone-15), Tinosorb M™ (methylene bis-benzotriazolyl tetramethylbutylphenol), tinosorb S™ (bis-ethylhexyloxyphenol methoxyphenyl triazine), Tinosorb A2B™ (tris-biphenyl triazine), Uvasorb HEB™ (diethylhexyl butamido triazone), Uvinul T 150™ (ethylhexyl triazone), and Uvinul A Plus™ (diethylamino hydroxybenzoyl hexyl benzoate).

In another embodiment the composition disclosed herein will form part of a wound dressing, bandage, patch, gauze, suture, surgical tape, or wipe.

In another embodiment, the composition disclosed herein further includes at least one anti-cancer drug or other anti-cancer agent.

The foregoing paragraphs have been provided by way of general introduction, and are not intended to limit the scope of the following claims. The described embodiments, together with further advantages, will be best understood by reference to the following detailed description taken in conjunction with the accompanying drawings.

DETAILED DESCRIPTION OF THE INVENTION

The incidence of malignant melanoma has rapidly increased in the last two decades. As conventional therapies have limited efficacy due to resistance, non-mutually exclusive mutations, and adverse side effects, researchers have explored alternate therapies such as nanoclays. Nanoclays are nanosized natural materials originating from clay fraction of soil. In recent years nanoclays or clay nanoparticles have been received increasing attentions for their use as a drug carrier and additive for cancer treatment due to their high absorption, ability to engulf microbes, and low toxicity. The specific nanoclays used herein are Palygorskite (PFl-1) and Na-montmorillonite (SWy-3). The effects of pFI-1 and SWy-3 on human melanoma cell proliferation and viability are described. A three-day dosage response and a five-day timing course analyses were conducted. The results demonstrated that nanoclay treatments reduced melanoma cell proliferation and cell viability in dosage dependent manor. This shows the important role of nanoclay as inhibitor of melanoma cell proliferation and potential use for cancer therapy (see examples herein below).

Nanoclays are nanoparticles of layered mineral silicates. Depending on chemical composition and nanoparticle morphology, nanoclays are organized into several classes such as montmorillonite, bentonite, kaolinite, hectorite, and halloysite. In some embodiments, one or more of types of nanoclays, such as those described above and herein are used. Nanoclays, including organically modified nanoclays, are commercially available, such as from Sigma Aldrich and are incorporated by reference.

Clays are a distinguished from other fine-grained earth deposits and are grouped into distinct classes such as kaolinites, illites, or smectites. Clays based on silicates form a large class, where the basic structural unit for silicate clays is a $SiO_4$ tetrahedron in which $Si^{4+}$ is located at the center and four $O^{2-}$ are positioned at the apices. The tetrahedral structures can be linked together by sharing four $O^{2-}$ ions and together can form a variety of more complex structures including rings (cyclosilicates), chains (inosilicates), sheets (phyllosilicates) and three dimensional arrangements (tectosilicates). Tetrahedra, e.g., $SiO_4$ $_{and}$ octahedral, e.g., $Al_2O_3$ are common structural components in many mineral structures.

In one embodiment, the clay for use in the methods described herein is a phyllosilicate clay. Phyllosilicate clays contain both tetrahedral and octahedral sheets, and are further categorized according to composition and packing arrangement. In some embodiments, the clay material is a phyllosilicate selected from the group consisting of kanemite, kenyaite, magadiite and makatite. In some embodiments, the phyllosilicate is selected from the group consisting of allophane (hydrated aluminum silicate); apophyllite (hydrated potassium sodium calcium silicate hydroxide fluoride); bannisterite (hydrated potassium calcium manganese iron zinc aluminum silicate hydroxide); carletonite (hydrated potassium sodium calcium silicate carbonate hydroxide fluoride); cavansite (hydrated calcium vanadate silicate); chrysocolla (hydrated copper aluminum hydrogen silicate hydroxide); clay minerals (described in detail below); delhayelite (hydrated sodium potassium calcium aluminum silicate chloride fluoride sulfate); elpidite (hydrated sodium zirconium silicate); fedorite (hydrated potassium sodium calcium silicate hydroxide fluoride); franklinfurnaceite (calcium iron aluminum manganese zinc silicate hydroxide); franklinphilite (hydrated potassium manganese aluminum silicate); gonyerite (manganese magnesium iron silicate hydroxide); gyrolite (hydrated calcium silicate hydroxide); kanemite; kenyaite; leucosphenite (hydrated barium sodium titanium boro-silicate); magadiite; makatite; micas such as biotite(potassium iron magnesium aluminum silicate hydroxide fluoride), lepidolite (potassium lithium aluminum silicate hydroxide fluoride), muscovite(potassium aluminum silicate hydroxide fluoride), paragonite (sodium aluminum silicate hydroxide), phlogopite(potassium magnesium aluminum silicate hydroxide fluoride) and zinnwaldite (potassium lithium aluminum silicate hydroxide fluoride); minehillite (hydrated potassium sodium calcium zinc aluminum silicate hydroxide); nordite (cerium lanthanum strontium calcium sodium manganese zinc magnesium silicate); octosilicate; pentagonite (hydrated calcium vanadate silicate); petalite (lithium aluminum silicate); prehnite (calcium aluminum silicate hydroxide); rhodesite (hydrated calcium sodium potassium silicate); sanbornite (barium silicate); serpentines such as antigorite(magnesium iron silicate hydroxide), clinochrysotile (magnesium silicate hydroxide), lizardite (magnesium silicate hydroxide), orthochrysotile (magnesium silicate hydroxide) and serpentine(iron magnesium silicate hydroxide); wickenburgite (hydrated lead calcium aluminum silicate); and zeophyllite (hydrated calcium silicate hydroxide fluoride).

Clay minerals include chlorites such as baileychlore (zinc iron aluminum magnesium silicate hydroxide), chamosite (iron magnesium aluminum silicate hydroxide oxide), the generalized mineral chlorite, clinochlore (a chromium variety kaemmererite) (iron magnesium aluminum silicate hydroxide), cookeite (lithium aluminum silicate hydroxide), nimite (nickel magnesium iron aluminum silicate hydroxide), pennantite (manganese aluminum silicate hydroxide), penninite (iron magnesium aluminum silicate hydroxide) and sudoite (magnesium aluminum iron silicate hydroxide); glauconite (potassium sodium iron aluminum magnesium silicate hydroxide); illite (hydrated potassium aluminum magnesium iron silicate hydroxide); kaolinite(aluminum silicate hydroxide); montmorillonite (hydrated sodium calcium aluminum magnesium silicate hydroxide); palygorskite (hydrated magnesium aluminum silicate hydroxide); pyrophyllite (aluminum silicate hydroxide); sauconite (hydrated sodium zinc aluminum silicate hydroxide); talc(magnesium silicate hydroxide); and vermiculite (hydrated magnesium iron aluminum silicate hydroxide). For example, palygorskite or attapulgite is a magnesium aluminium phyllosilicate with formula $(Mg,Al)_2Si_4O_{10}(OH)4(H_2O)$ which occurs in a type of clay soil common to the Southeastern United States. Attapulgite clays are a composite of smectite and palygorskite. Smectites are expanding lattice clays of which bentonite is a commonly known generic name for smectite clays. The palygorskite component is an acicular bristle-like crystalline form which does not swell or expand. Attapulgite forms gel structures in fresh and salt water by establishing a lattice structure of particles connected through hydrogen bonds.

Palygorskite or attapulgite is a magnesium phyllosilicate with formula $(Mg,Al)_2Si_4O_{10}(OH)\cdot 4(H_2O)$ that occurs in a type of clay soil common to the Southeastern United States. It is one of the types of fuller's earth. Some smaller deposits of this mineral can be found in Mexico, where its use is tied to the manufacture of Maya blue in pre-Columbian times. It is a phyllosilicate having a repeating unit formula of $(Mg, Al)_2Si_4O_{10}(OH)\cdot 4(H_2O)$. In some embodiments, one or more types of palygorskite are used. Members of the palygorskite-sepiolite group, which may be used in some embodiments of the invention, include palygorskite, falcondoite, intersilite, kalifersite, loughlinite, raite, sepiolite, tuperssuatsiaite and yofortierite; see hypertext transfer protocol secure: //www.researchgate.net/publication/251469-983_The_Structures_and_Microtextures_of_the_Paly gorskite-Sepiolite_Group_Minerals (incorporated by reference, last accessed Jun. 2, 2019).

In some embodiments, less than 5, 4, 3, 2, 1 or 0.5 wt % or no palygorskite is incorporated into the nanoclay component based on the total weight of the nanoclay component. In some embodiments a nanoclay as disclosed herein may contain 1, 2, 5, 10, 20, 30, 40, 50, 60, 70, 80, 90, 95, 99 or 100% of a palygorskite such as a palygorskite having the formula $(Mg,Al)_2Si_4O_{10}(OH)\cdot 4(H_2O)$ based on the total weight of the nanoclay. Attapulgite, unlike bentonite, will form gel structures in salt water and is used in special salt water drilling mud for drilling formations contaminated with salt. Palygorskite particles can be considered as charged particles with zones of + and − charges. It is the bonding of these alternating charges that allow them to form gel suspensions in salt and fresh water. Attapulgite clays found in the Meigs-Quincy district are bundles of palygorskite clay particles between 2 and 3 micrometers long and below 3 nanometers in diameter. The bundles are surrounded by a matrix of smectite clays which are slightly swellable. Dry process grades contain up to 25% non-attapulgite material in the form of carbonates and other mineral inclusions.

Montmorillonite is a very soft phyllosilicate group of minerals that form when they precipitate from water solution as microscopic crystals, known as clay. It is named after Montmorillon in France. Montmorillonite, a member of the smectite group, is a 2:1 clay, meaning that it has two tetrahedral sheets of silica sandwiching a central octahedral sheet of alumina. Montmorillonite has a flaky particle configuration with a high surface area. The particles are plate-shaped with an average diameter around 0.8, 0.9, 1, 1.1 or 1.2 µm and a thickness of about 0.9, 0.91, 0.92, 0.93, 0.94, 0.95, 0.96, 0.97, 0.98, 0.99, 1.0, 1.01, or 1.02 nm; magnification of about 25,000 times, using an electron microscope, is required to see individual clay particles. Members of this group include saponite. It has a repeating unit formula of $(Na,Ca)_{0.33}(Al,Mg)_2(Si_4O_{10})(OH)_2\cdot nH_2O$. In some embodiments, one or more types of montmorillonite are used. Clays of the montmorillonite group include those of the montmorillonite-beidelite series, notronite, the saponite-hectorite series, and others described by hypertext transfer protocol secure://_pubs.usgs.gov/pp/0205b/report.pdf (last accessed May 31, 2019). In some embodiments, less than 5, 4, 3, 2, 1 0.5 or <0.5 wt % or no montmorillonite is incorporated into the nanoclay component based on the total weight of the nanoclay component. In some embodiments a nanoclay as disclosed herein may contain 1, 2, 5, 10, 20, 30, 40, 50, 60, 70, 80, 90, 95, 99 or 100% of a montmorillonite such as a montmorillonite having the formula $(Na,Ca)_{0.33}(Al,Mg)_2(Si_4O_{10})(OH)_2\cdot nH_2O$ based on the total weight of the nanoclay. Typically, about 100% of the dry weight of a montmorillonite used in the invention will be made up of a material having the formula $(Na,Ca)_{0.33}(Al,Mg)_2(Si_4O_{10})(OH)_2\cdot nH_2O$ and about 100% of the dry weight of a palygorskite clay used in the invention will have a formula of $(Mg,Al)_2Si_4O_{10}(OH)\cdot 4(H_2O)$. It is unnecessary for anticancer activity for the nanoclays used in the invention contain further active ingredients. In some embodiments, due to weak bonding between Na cations and clay particles, high surface area of the individual clay particles in Na-rich clays is readily available for the interaction with cells and its biological environment.

Bentonite is an absorbent clay consisting mostly of montmorillonite. The different types of bentonite are each named after the respective dominant element, such as potassium (K), sodium (Na), calcium (Ca), and aluminium (Al). In some embodiments of the invention less than 5, 4, 3, 2, 1 0.5 or <0.5 wt % or none of one or more forms of bentonite is incorporated into the nanoclay component based on the total weight of the nanoclay component.

Sepiolite is opaque and off-white, grey or cream color, breaking with a conchoidal or fine earthy fracture, and occasionally fibrous in texture. Due to the fact it can be readily scratched with the finger nail, its hardness is ranked at about 2 on the Mohs scale. The specific gravity varies from 0.988 to 1.279, but the porosity of the mineral may lead to error. Sepiolite is a hydrous magnesium silicate having the chemical formula $Mg4Si_6O_{15}(OH)_2\cdot 6H_2O$. In some embodiments of the invention less than 5, 4, 3, 2, 1, 0.5 or <0.5 wt % or no sepiolite is incorporated into the nanoclay component based on the total weight of the nanoclay component. Sepiolite has got rectangular channels while palygorskite has square channels. This makes palygorskite much more porous as compared to sepiolite for equivalent volume/surface area.

Treated clays. In some embodiments phyllosilicate particles in a clay may be treated with an organic material to intercalate organic molecules between adjacent, planar silicate layers. For example, treatment can be with an organic material such as silane coupling agents; quaternary ammonium compounds; monomeric compounds having an electrostatic functionality selected from the group consisting of amines, amides and mixtures thereof; monomeric compounds having a functionality selected from the group consisting of hydroxyl, aromatic rings, carbonyl, carboxylic acid, polycarboxylic acid, aldehydes, ketones, amines, amides, ethers, esters and combinations thereof; and so forth. It is not required that a nanoclay be incorporated into a polymer material, admixed with anticancer drugs such as a heteroaryl pyrimidine derivative, with gold or other noble metal nanoparticles, or with particular excipients such as hydrogel which neutralizes charges on surfaces or edges of clay particles.

In some embodiments one or more of these clays or clay minerals may be incorporated into a composition for treatment or prophylaxis of skin cancer. In other embodiments, one or more of these clays may be omitted from a composition for treatment or prophylaxis of skin cancer.

Nanoclay particle sizes. A skilled artisan will appreciate that clay can be sized by sieving or by air classification to achieve a desired average particle size. A skilled artisan in the relevant field will appreciate that any representative sample of clay will be polydisperse in size, yet the art provides several approaches for expressing the average size, or diameter, of particles in a population. For example, an average particle size, or uniform particle size, may in some embodiments intend that a representative sample of the clay when passed through a sieve of a certain mesh size retains a majority (greater than 50%) of the clay sample.

Size fractionation (wet and dry) of a representative sample of a given clay can be done as follows. Wet state fractionation involves removal of cementing and flocculating materials in the sample using sodium acetate buffer (pH 5). Organic matter in the sample is removed using 30% hydrogen peroxide. The sample is then dispersed with 50 mL of pH 10 sodium carbonate solution. The sand fraction (>53 µm) is separated using a 53 µm sieve. The clay fraction (<2 µm) is separated from the silt fraction (2-53 µm) by centrifugation using pH 10 sodium carbonate as dispersant. Sand and silt weights are recorded after drying at 105° C. overnight. The clay suspension is flocculated with sodium chloride and then dialyzed until the electrical conductivity measurement are close to the values of deionized water (<2 pS/cm).

Air dry fractionation of clay can be done using, for example, an Octagon 200 sieve shaker (Endecotts), and weight average particle size determined in accord with the manufacturer's instructions. For example, the percentage of particles with greater than 100 μm size, between 45, 50, 55, 60, 65, 70, 75, 90, 85, 90, to 100 μm size, and less than 45 μm size is calculated. In one embodiment, the montmorillonite clay comprises a majority (i.e., 51%, based on weight percent) of particles with a dry state fractionation size of between about 50, 100, 150, to 200 μm.

In other embodiments, the montmorillonite or palygorskite clay is comprised of a particles wherein at least 60%, 70%, 75% or 80% of the particles have a dry state fractionation size of between about 50, 100, 150 to 200 μm. In another embodiment, montmorillonite or palygorskite clay comprises a majority of particles with a wet state fractionation size of less than 2 μm. In another embodiment, the average particle size of the clay in a dry state is less than about 200 μm, or less than about 100 μm, or less than about 80 μm. In other embodiments, the average particle size of the clay is between 5, 10, 20, 50, 100, 150-200 μm or between 5, 10, 15, 20, 25, 30, 35, 40, 45-50 μm.—Preferably, a particle size of clay for treating skin cancer or melanoma should be as small as possible so as to maximize surface interaction of the clay particles with cells and the biological environment.

Nanoclay compositions. A nanoclay can be formulated with one or more pharmaceutical excipients to provide a composition for administration to a patient in need of treatment. A therapeutic composition may contain any amount of a nanoclay that reduces the proliferation or viability of a cancer cell, such as a skin cancer cell, especially a melanoma cell.

Any effective concentration of nanoclay may be used. For example, a nanoclay composition may contain by weight <0.001, 0.001, 0.002, 0.005, 0.01, 0.02, 0.05, 0.1, 0.2, 0.5, 1, 2, 5, 10, 20, 50, 60, 70, 80, 90, or 100% by weight of one or more nanoclays as disclosed herein, preferably, a palygorskite and/or a montmorillonite nanoclay. These ranges include all intermediate values and subranges.

In some embodiments, an amount of nanoclay, such as palygorskite and/or montmorillonite, ranges from about 1, 2, 3, 4, 5, 6, 7, 8, 9, 10, 20, 50, 100, 200, 300, 400, 500, 600, 700, 800, 900, 1,000 or >1,000 μg/ml based on the total weight of the composition, advantageously about 1-200 μg/ml or about 2-20 μg/ml.

The preparation of pharmaceutically acceptable carriers and formulations suitable for containing nanoclay is described in *Remington's Pharmaceutical Sciences,* 21st Edition, ed. University of the Sciences in Philadelphia, Lippincott, Williams & Wilkins, Philadelphia Pa., 2005, which is incorporated herein by reference in its entirety. By way of general example, from about <1, 1, 2, 5, 10, 20, 50, 100, 200, 500, 1,000 μg or 1, 2, 5, 10, 50, 100 or >100 mg of one or more nanoclays per kg body weight may be administered. Preferred dosages for topical administration range from about 10 to 40 μg/ml or about 20 μg/ml, for intradermal administration from about 5 to 20 μg/ml or about 10 μg/ml, and from about 2.5 to 10 μg/ml or about 5 μg/ml. These ranges include all intermediate values and subranges.

A composition may have an acidic or basic pH, such as a pH ranging from 1, 2, 3, 4, 5, 6, 7, 8, 9, 10, 11, 12, 13 to 14 (or any intermediate value within this range), preferably from 3 to 9, more preferably from 5.5 to 8.5. It may match or coordinate to the pH of the skin (e.g., from pH 4 to 7.0, preferably about pH 5) or other tissue to which it is applied or vary upward or downward by about 0.1, 0.2, 0.3, 0.4, 0.5, 0.6, 0.7, 0.9, 1.0, 1.5 or 2.0 pH units from a neutral pH or from the pH of skin, hair, nails, mucosal, or other tissue to which it is applied.

Compositions, including topical compositions, may be prepared as solutions, serums, lotions, creams, pastes, ointment/salves, gels, aerosols, foams and other conventional formulations using known carriers for such applications. Such formulations may be administered directly, for example, applied directly to a dermal site such as a site suspected of containing skin cancer or melanoma cells. It may be applied by hand or mechanically, such as by spraying or by impregnation into a bandage, dressing, or adhesive or non-adhesive gel or other covering.

A composition containing one or more nanoclays, such as palygorskite and/or montmorillonite, may contain stabilizers, preservatives, humectants, regreasing agents, solvents or auxiliaries to improve efficacy and penetration into the dermis or other tissue. Penetration-enhancing compounds include propylene glycol, polyethylene glycol, dimethylsulphoxide, decylmethylsulphoxide, azoles, N-methylpyrrolidone, diethyltoluamide, ethanol, isopropyl myristate, isopropyl palmitate, oleic acid and its esters, medium-chain triglycerides, dimethyl isosorbitol, 2-octyldodecanol, branched fatty acids, benzyl alcohol, urea, salicylates and surfactants. A nanoclay composition may contain an oil, grease or hydrocarbon that is solid at room temperature. An oil is any nonpolar chemical substance that is a viscous liquid at ambient temperatures and is both hydrophobic (does not mix with water, literally "water fearing") and lipophilic (mixes with other oils, literally "fat loving"). Oils have a high carbon and hydrogen content and are usually flammable and surface active. A grease is any petroleum product or fat (including cooking fat) that is a soft solid at room temperature. As used herein the term "consisting essentially of" when describing a composition containing one or more clays of the invention, excludes anticancer drugs as well as metallic materials, such as gold or noble metal nanospheres, used for phototherapy. Unless otherwise specified, it does not exclude excipients or carriers with no or substantially no independent anticancer or antimelanoma activity, such as buffers, bulking agents, penetration enhancers, or other excipients or ancillary materials that stabilize or adapt the nanoclay for administration, which facilitate its delivery or persistence in a site containing cancer cells, or which otherwise improve the pharmacokinetic or pharmacodynamic properties of the at least one nanoclay as the sole or predominant active anticancer ingredient (e.g., responsible for >50, 60, 70, 80. 90, 95, 96, 97, 98, 99 or >99% of the anticancer activity).

Viscosity enhancers or thickeners can be included, for example to prevent a composition from spreading beyond the site of application. Thickeners include carbomer, hydroxypropyl methylcellulose, hydroxyethylcellulose, PVM/MA decadiene cross-polymer and acrylates.

In some embodiments, a nanoclay composition may contain hyaluronic acid, collagen, elastin, or other components of the skin, vitamins, amino acids, antioxidants or antibiotics. Such a composition may be used, for example, to facilitate healing of a site where skin cancer cells have been excised. Hyaluronic acid is a substance that is naturally present in the human body and may be extracted from rooster combs or made by recombinantly. Hyaluronic acid may be applied to the skin in combination with a nanoclay for healing surgical wounds around excised melanoma cells.

In other embodiments, a nanoclay composition may contain an antioxidant such as Vitamin A, C or E, cysteine, proline, hydroxyproline, lysine, glycine, thiols, thyoredoxins, glutathione, or enzymes like catalase or superoxide dismutase. Vitamins D or K may be included as well as the B vitamins. In some embodiments human or mammalian SODs such as Cu/Zn type SOD1 are used in a nanoclay composition. In other embodiments prokaryotic SODs may be used. One or more SODs may be used in combination with a nanoclay or other active ingredients in a nanoclay composition of the invention.

Spreading oils or emollients can be included in the nanoclay composition. One benefit for including such oils is for better distribution on surfaces, in particular on the skin. Spreading oils are understood as those oily liquids which are distributed particularly easily on the skin. Suitable spreading agents can include silicone oil, fatty acid esters, such as ethyl stearate, di-n-butyl adipate, hexyl laurate and dipropylene glycol pelargonate, esters of a branched fatty acid of medium chain length with saturated $C_{16}$-$C_{18}$ fatty alcohols, isopropyl myristate, isopropyl palmitate, caprylic/capric acid esters of saturated fatty alcohols of $C_{12}$-$C_{18}$ chain length, isopropyl stearate, oleyl oleate, decyl oleate, ethyl oleate, ethyl lactate, waxy fatty acid esters, such as synthetic duck uropygial gland fat, dibutyl phthalate, diisopropyl adipate, ester mixtures related to the latter and the like. Other elements that can be included are emollients, such diisopropyl adipate/isohexadecane dimethicone, occlusive agents, such as example cyclomethicone, trimethylsiloxysilicate, glycereth-26 or polyquaternium-7, emulsifiers, such as cetyl alcohol, stearyl, stearic acid, glyceryl stearate, propylene glycol isostearoyl-sodium isostearoyl, a lactylate, polyoxyethylene (100) stearate, skin conditioners, moisturizers, humectants, such as propylene glycol or glycerin, preservatives, such as phenoxyethanol and parabens, pH adjusting agents, surfactants, chelators, such as disodium EDTA or sodium citrate, tackifying agents, fragrances and other compounds.

A serum refers to a light, quickly absorbed composition that exposes and permits rapid application or uptake of an active ingredient by skin. It can be used as an alternative to heavier creams or lotions that contain occlusive, or airtight, moisturizing ingredients such as petrolatum or mineral oil that keep water from evaporating. Serums usually contain fewer lubricating and thickening agents, like nut or seed oils, than creams or lotions. Most serums are water-based or based on hydrophilic components, eliminating oils altogether. A serum may be formulated to contain a higher or lower concentration of nanoclay than a cream or lotion.

Lotions described herein include liquids or semi-liquid formulations that are generally lower in viscosity than a cream or gel. The lotions can be an oil-in-water or water-in-oil formulation stabilized by a surface-active agent and are usually suitable for application to skin, hair or nails. They may be in a form of an emulsion and include methylcellulose, sodium carboxymethyl-cellulose, and similar compounds or contain other ingredients such as those described herein for creams and other pharmaceutical compositions provided the combined amounts of the ingredients form a lotion.

Creams provided herein include liquids or semi-solid emulsions with a viscous consistency. Creams can be either oil-in-water or water-in-oil based formulations. Cream bases can be water soluble. Cream bases can contain the following components: (1) an oil phase, (2) an aqueous phase, and (3) an emulsifier. The oil phase can comprise petroleum jelly and a fatty alcohol, such as cetyl or stearyl alcohol. The aqueous phase can contain a humectant. The emulsifier can be a nonionic, anionic, cationic or amphoteric surfactant. In one embodiment, the oil phase includes, but is not limited to, cetyl alcohol, stearyl alcohol, stearic acid, liquid paraffin, and dimethicone.

Ointments/salves incorporating one or more nanoclays include semi-solid preparations that have petroleum jelly or their derivatives as a base. Petroleum jelly is a semi-solid mixture of hydrocarbons. As described in *Remington: The Science and Practice of Pharmacy*, 19th Ed. (Easton, Pa.: Mack Publishing Co., 1995), at pages 1399-1404, ointment bases can be grouped in four classes: oleaginous bases; emulsifiable bases; emulsion bases; and water-soluble bases. Oleaginous ointment bases include vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petroleum jelly. Emulsion ointment bases are either water-in-oil or oil-in-water emulsions, and include, for example, cetyl alcohol, glyceryl monostearate, lanolin, and stearic acid. An ointment may contain solid or encapsulated particles or emulsified and suspended particles of nanoclays. Black Ointment, or Ichthyol Salve, also called Drawing Salve may be modified to contain a nanoclay.

Pastes incorporating a nanoclay can contain, in addition to an ointment or cream base, high amounts of pulverulent constituents, such as zinc oxide, talc, starch or titanium dioxide. In one embodiment, the paste is selected from the group comprising fatty pastes or single-phase aqueous gels. The fatty paste includes petroleum jelly, hydrophilic petroleum jelly, or other similar compounds. The single-phase aqueous gel can incorporate carboxymethylcellulose or similar compounds. A paste may contain solid or encapsulated particles or emulsified and suspended particles of a nanoclay.

Gels provided herein include semi-solid suspensions that contain nanoclay. The gels can be single- or two-phase systems. The gels can be oil or liquid based. Single-phase gels can contain small organic macromolecules distributed substantially uniformly throughout a liquid, such that the there is no boundary between the macromolecules and liquid. The liquid can be aqueous, but also contain an alcohol, and, optionally, an oil. Single-phase gels can be made from synthetic macromolecules or from natural gums. Two-phase gels can include a network of small, discrete particles. In one embodiment, two-phase gels are thixotropic. In one embodiment, the organic macromolecules include crosslinked acrylic acid polymers such as the "carbomer" family of polymers (i.e., carboxypolyalkylenes). The organic macromolecules can also be hydrophilic polymers such as polyethylene oxides, polyoxyethylene-polyoxypropylene copolymers and polyvinyl alcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In another embodiment, the organic macromolecules having a stabilizing action include long-chain linear high molecular weight polysaccharides with a molecular weight of more than one million. In another embodiment, a uniform gel can be prepared by adding dispersing agents such as alcohol or glycerin. In another embodiment, the organic macromolecules can be dispersed by trituration, mechanical mixing or stirring, or combinations thereof. In another embodiment, the liquid can be either water or all water-miscible solvents. Examples of applicable solvents include alkanols, such as ethanol and isopropyl alcohol, benzyl alcohol, propylene glycol and similar solvents.

Hydrogels containing cross-linked insoluble starch or carboxymethylcellulose polymers nanoclay. Care must be taken that ingredients in hydrogels or other compositional forms described herein do not neutralize the skin cancer inhibiting properties of nanoclays.

Hydrocolloid dressings containing polymers such as gelatin, pectin and cellulose and one or more nanoclays and which form a waterproof adhesive dressing may be used to treat a tissue in need of treatment, such as a tissue suspected of containing skin cancer cells.

Alginate dressings containing one or more nanoclays may also be used for skin disorders, burns or wounds or other tissues in need of treatment with nanoclays. These tend to be highly absorbent and are available in two forms; calcium alginate and calcium sodium alginate. The use of alginate dressings as hemostatic agents was reported both in vitro and in clinical studies. The selection of an alginate dressing is usually to manage wound exudate, as it is claimed that they can absorb 15-20 times their own weight in wound fluid. The alginate forms a gel when it comes into contact with a target surface such as skin or skin containing a surgical wound after removal of melanoma cells. It can be used in granulating, epithelializing, and cavity wounds.

Aerosols as provided herein include nanoclay-containing products packaged under pressure and contain ingredients that are released upon activation of an appropriate valve system. Aerosols include all self-contained pressurized products, such as fine mists of spray or foam, that are emitted from a pressurized container containing a propellant, foams, or semisolid liquids. They may also be emitted by an unpressurized atomizer that is pressurized by a hand-operated pump rather than by stored propellant. In one embodiment, the aerosol comprises a container, a propellant, a concentrate containing an active ingredient, a valve (which may be a metered valve), and an actuator. The nature of these components determines characteristics such as delivery rate, foam density, and fluid viscosity. In another embodiment, the aerosol is a two-phase formulation comprising a gas and liquid. In another embodiment, the aerosol is a three-phase formulation comprising a gas, liquid, and suspension or emulsion of active ingredients. In this formulation, suitable excipients, such as wetting agents and/or solid carriers such as talc or colloidal silicas are included. In another embodiment, the propellant is liquefied or vaporized. In another embodiment, a solvent can be the propellant or a mixture of the propellant and co-solvents such as alcohol and polyethylene glycols. In another embodiment, the propellant is selected from the group comprising a spray, foam, or quick-breaking foam. In another embodiment, spray formulations are aqueous solutions in a container having a spray means, such as an atomizer or nebulizer. An aerosol may contain solid or encapsulated particles, emulsified and suspended particles, or liquid or atomized droplets containing one or more nanoclays.

Foams. In some embodiments, one or more nanoclays is delivered to the body while in a foam state, such as stable foam, for example, that is produced with or without a propellant. For example, the extract may be contained in a shaving foam and used for preventing bacterial infection of nicks, cuts or abrasions associated with shaving. In some versions, a foam is dispensed from a dispenser such as a propellant-free dispenser with pumping action to create the foam from a composition in a foamable carrier, and then applied to a wipe or other substrate, or applied to the hand of the user or otherwise delivered to the skin. Propellant-driving foam generators may also be used to deliver the composition in the form of a foam. Active ingredients in a foam may be dispensed for subsequent placement on a dry wipe, a pre-moistened wipe, or other soft, flexible applicator (e.g., an object about 3-fingers wide or 4 to 10 cm wide) or other object to be used for application of the foam-based composition to the skin. The foam can be a non-propellant foam. A foam with a suitable stiffness of yield stress can be applied to the skin in any manner for sustained adherence and contact with the body. Examples of foam-based systems are described in U.S. Pat. No. 6,818,204, "Stable Foam for Use in Disposable Wipe," herein incorporated by reference. This patent involves the use of compatible surfactants, e.g., nonionic, anionic, amphoteric, for use in human hygienic products. The surfactant should be capable of forming a foam when mixed with air in a finger actuated, mechanical pump foamer. Such surfactants are said to include, without limitation, those which do not irritate mucous membranes such as polyethylene 20 cetyl ether (Brij 58)™, a nonionic surfactant; sodium lauroyl sarcosinate (Hamposyl L-30)™, sodium lauryl sulfoacetate (Lathanol LAL)™ and sodium laureth sulfate (Sipon ESY)™, anionic surfactants; lauramidopropyl betaine (Monateric LMAB™), an amphoteric surfactant, as well as polysorbate 20, TEA-cocoyl glutamate, disodium cocoamphodiacetate and combinations thereof. Typically, a surfactant is present in an amount from about 2% to about 35% by weight, or from about 5% to about 15% by weight (or any intermediate value or subrange).

At least one foam stabilizing agent may be present in some foamable embodiments. Suitable foam stabilizing agents may include, without limitation, natural or synthetic gums such as xanthan gum, polyalkylene glycols such as polyethylene glycol, alkylene polyols such as glycerine and propylene glycol and combinations thereof. Typically, the foam stabilizers may be present in an amount from about 0.10% to about 5%, or from about 2% to about 4%. In the Lapidus patent (U.S. Pat. No. 6,818,204), alkylene polyols are said to be typically employed in amounts from about 0.1% to about 10%, gums are employed in amounts ranging from about 0.05% to about 1%, and/or polyalkylene glycols are present in amounts ranging from about 0.05% to about 2%. The ranges above include all intermediate values and subranges.

A foam may be produced using the F2 Finger Pump Foamer™. manufactured by AirSpray International Inc. of Pompano Beach, Fla. Such a spring-loaded valve system operates without the use of gas propellants or the like. Upon actuation, precise amounts of air and liquid are mixed, and a foam capable of maintaining its structure for a substantial length of time is dispensed. In addition, the dispenser can deliver a variable amount of foam, thereby reducing waste. Details of exemplary propellantless defoamers are described in U.S. Pat. Nos. 5,443,569 and 5,813,576 herein incorporated by reference. Foams and other compositions described herein containing the nanoclay components disclosed herein may be dispensed to surfaces containing skin cancer cells or suspected to containing skin cancer cells or may be used prophylactically on surgical wounds left after removing skin cancer cells such as after removal of a melanoma lesion and a margin of cells around the lesion.

Bioadhesive compositions are particularly suitable for treating skin cancers such as melanoma. Patches comprising a polymer and the clay, where the polymer becomes adhesive in the presence of body fluids, are known in the art.

Nonlimiting examples of biocompatible polymers that can be used to make a bioadhesive composition including a nanoclay include polyethers, such as polyoxyalkylene block copolymers; cellulosic polymers (including hydroxypropylmethyl cellulose, hydroxymethyl cellulose, hydroxypropyl cellulose, methyl cellulose and ethylhydroxyethyl cellulose); gelatin; polyethylene glycol; polyacrylic acid (such as Carbopol™ gel); and glycerol (glycerin). More than one of these exemplary polymers may be included in the composition to provide the desired characteristics and other biocompatible polymers or other additives may also be included in the composition to the extent the inclusion is not inconsistent with performance requirements of the composition.

The composition may also include conventional additives such as adhesive agents, antioxidants, crosslinking or curing agents, pH regulators, pigments, dyes, refractive particles, conductive species, antimicrobial agents, active agents and permeation enhancers. In those embodiments wherein adhesion is to be reduced or eliminated, conventional detackifying agents may also be used. These additives, and amounts thereof, are selected in such a way that they do not significantly interfere with the desired chemical and physical properties of the composition such as an ability for the nanoclay component to recognize and interact with cancer cells.

Other non-limiting examples of suitable excipients, diluents, and carriers include: fillers and extenders such as starch, sugars, mannitol, and silicic derivatives; binding agents such as carboxymethyl cellulose and other cellulose derivatives, alginates, gelatin, and polyvinyl pyrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as acetyl alcohol, glycerol monostearate; carriers such as propylene glycol and ethyl alcohol, and lubricants such as talc, calcium and magnesium stearate, and solid polyethyl glycols. In some embodiments a nanoclay composition as disclosed herein may contain, or be selected not to contain, one or more of mesoporous silica, aluminosilicate, mesoporous alumina, mesoporous clay, mesoporous metal oxide, mesoporous metal hydroxide, and mesoporous polymer. In some embodiments, a nanoclay composition as disclosed herein will not contain additional anticancer agents or drugs. Preferably, an additive is selected that does not compromise the interaction of a nanoclay with cancer cells, for example, by neutralizing charge of other physical qualities of the nanoclay and reducing its ability to bind to or interact with a cancer cell.

Sunscreens are used to prevent melanoma and are made more effective by incorporation of a nanoclay component according to the invention which inhibits growth of melanoma or other skin cancer cells. In the past, use of sunscreens with a sun protection factor (SPF) rating of 50 or higher on exposed areas were recommended to reduce risk of developing melanoma; as older sunscreens more effectively blocked UVA with higher SPF. Currently, newer sunscreen ingredients (avobenzone, zinc oxide, and titanium dioxide) effectively block both UVA and UVB even at lower SPFs. Sunscreen also protects against squamous cell carcinoma, another skin cancer. A sunscreen may have an SPF ranging from 1, 2, 5, 10, 20, 30, 40, 50 to >50, preferably from about 30 to 50.

Skin cancers include basal cell skin cancer, squamous cell carcinoma and malignant melanoma. The nanoclay based method disclosed herein may be used to inhibit or reduce viability of skin cancer cells, especially melanoma cells. In an alternative embodiment, the method as disclosed herein may be used to treat other types of cancers by bringing them into contact with a nanoclay.

Melanoma, also known as malignant melanoma, is a type of cancer that develops from the pigment-containing cells known as melanocytes. Melanomas typically occur in the skin, but may rarely occur in the mouth, intestines, or eye. In women, they most commonly occur on the legs, while in men they are most common on the back. Sometimes they develop from a mole with changes such as an increase in size, irregular edges, change in color, itchiness, or skin breakdown. Using sunscreen and avoiding UV light may prevent melanoma. Treatment is typically removal by surgery.

Melanoma staging. Various stages of melanoma are recognized: Stage 0: Melanoma in situ (Clark Level I), 99.9% survival; Stage I/II: Invasive melanoma, 89-95% survival; T1a: Less than 1.0 mm primary tumor thickness, without ulceration, and mitosis <1/mm$^2$, T1b: Less than 1.0 mm primary tumor thickness, with ulceration or mitoses ≥1/mm$^2$, T2a: 1.01-2.0 mm primary tumor thickness, without ulceration; Stage II: High risk melanoma, 45-79% survival, T2b: 1.01-2.0 mm primary tumor thickness, with ulceration, T3a: 2.01-4.0 mm primary tumor thickness, without ulceration, T3b: 2.01-4.0 mm primary tumor thickness, with ulceration, T4a: Greater than 4.0 mm primary tumor thickness, without ulceration, T4b: Greater than 4.0 mm primary tumor thickness, with ulceration; Stage III: Regional metastasis, 24-70% survival, N1: Single positive lymph node, N2: Two to three positive lymph nodes or regional skin/in-transit metastasis, N3: Four positive lymph nodes or one lymph node and regional skin/in-transit metastases; and Stage IV: Distant metastasis, 7-19% survival, M1a: Distant skin metastasis, normal LDH, M1b: Lung metastasis, normal LDH, M1c: Other distant metastasis or any distant metastasis with elevated LDH. A subject having a melanoma at any of the stages described above may be treated as disclosed herein.

Melanoma genetics. Large scale studies such as The Cancer Genome Atlas have characterized recurrent somatic alterations likely driving initiation and development of cutaneous melanoma. The most frequent mutation occurs in the 600th codon of BRAF (50% of cases). BRAF is normally involved in cell growth and this specific mutation renders the protein constitutively active and independent of normal physiological regulation, thus fostering tumor growth. RAS genes (NRAS, HRAS and KRAS) are also recurrently mutated (30% of TCGA cases) and mutations in the 61st or 12th codons trigger oncogenic activity. Loss-of-function mutations often affect tumor suppressor genes such as NF1, TP53 and CDKN2A. BRAF, RAS and NF1 mutations are remarkably mutually-exclusive, as they occur in different subsets of patients. Assessment of mutation status can therefore improve patient stratification and inform targeted therapy with specific inhibitors. In some cases (3-7%) mutated versions of BRAF and NRAS undergo copy number amplification. A subject having a melanoma with any of these genetic alterations or features may be treated as disclosed herein.

Adjunct melanoma therapies. In addition to the methods disclosed herein, a subject may be treated with one or more conventional therapies, such as by surgery including Mohs surgery and double scalpel" peripheral margin controlled excision method; radiation; adjuvant therapy, such as with interferon; chemotherapy, such as with dacarbazine, temozolomide, nabpaclitaxel, paclitaxel, cisplatin, carboplatin or vinblastin; targeted therapy such as with inhibitors of BRAF, C-Kit or NRAS. BRAF inhibitors include vemruafenib and dabrafenib, MEK inhibitors include trametinib; by immunotherapy such as treatment with a cytokine (e.g., cytokines IL-2, IFN-α, aldesleukin/Proleukin) or by adoptive transfer of tumor-specific T cells, or by administration of an immune checkpoint inhibitors like anti-CTLA-4 monoclonal antibodies (e.g., ipilimumab, tremelimumab, Nivolumab (Opdivo) or Pembrolizumab (Keytruda), tol-like receptor agonists, anti-PD1- or PD-L1 antibodies (pembrolizumab, pidilizumab, and nivolumab).

Time and form of administration. According to the disclosed methods, compositions used herein can be administered to a patient prior to, concurrently with, or after a treatment for melanoma. In an example, the nanoclay composition is administered at the same time as, within 1, 2, 3, or 4 hours of, or on the same day as the treatment, and then for 1, 2, 3, 4, 5, 6, 7, 14, 21, 28 or >28 days thereafter (e.g., 1, 2, 3, 4 or >4 times per day). For example, a nanoclay composition as disclosed herein may be applied to skin after surgical removal of melanoma cells or surgical removal of a margin of cells around a suspected lesion.

The compositions can be administered to a patient by any acceptable manner known in the art, including topically (e.g., by gel, rinse, lozenge, cream, ointment, or patch), orally (e.g., by tablet, capsule, lozenge, cream, ointment, or patch), onto a mucous membrane, subcutaneously, intradermally, intralesionally, into a skin cancer nodule, intramuscularly, or intravenously (e.g., for disseminated or metastasized melanoma).

EXAMPLES

Nanoclay Suspension Preparations. Suspensions of two different nanoclays were made: pFI-1 (Palygorskite; (Mg, Al)$_2$Si$_4$O$_{10}$(OH)·4H$_2$O) and SWy-3 (Na-rich Montmorillonite; (Na,Ca)$_{0.33}$(Al, Mg)$_2$(Si$_4$O$_{10}$). Clays used in the examples herein are described in detail below.

Palygorskite(Attapulgite) PFl-1
ORIGIN: Hawthorne formation (miocene)
County of Gadsden, State of Florida, USA
LOCATION: SE 1/4 NW 1/4 sec. 10, T 3 N, R 3 W., topographic map Dogtown, Fla. (7.5'), Collected at the Luten mine from the first foot of claybed after stripping of overburden, Oct. 13, 1972.
CHEMICAL COMPOSITION (%): SiO$_2$: 60.9, Al$_2$O$_3$: 10.4, TiO$_2$: 0.49, Fe$_2$O$_3$: 2.98, FeO: 0.40, MnO: 0.058, MgO: 10.2, CaO: 1.98, Na$_2$O: 0.058, K$_2$O: 0.80, F: 0.542, P$_2$O$_5$: 0.80, S: 0.11, Loss on heating: −550° C.: 8.66; 550-1000° C.: 1.65.
CATION EXCHANGE CAPACITY (CEC): 19.5 meq/100 g
SURFACE AREA: N2 area: 136.35+/−0.31 m$^2$/g
THERMAL ANALYSIS: DTA: endotherm at 170° C., exotherm at 905° C., desorption of water; 230-300, desorption of adsorbed water; 495° C.; 550° C., dehydroxylation; 840° C. TG: Loss of absorbed water 12.96% (theory 14%), loss of structural water 5.52%.
INFRARED SPECTROSCOPY: The spectrum indicates fairly pure attapulgite. A trace of quartz is detectable (780 and 800 cm$^{-1}$). The spectrum shows considerable shifts upon drying of the sample in the OH stretching region (3000-3700 cm$^{-1}$) and in the Si—O stretching region (1000-1200 cm$^{-1}$) These shifts are reversible.
STRUCTURE: (Mg·33Ca·62 Na·04 K·13)[A11.50 Fe(III)· 52 Fe(II)·01 Mn·01 Mg1.91Ti·06][Si7.88 Al·22]O20 (OH)4, Octahedral charge: −1.87, Tetrahedral charge: −0.22, Interlayer charge: −2.09, Unbalanced charge: 0.00.

Na-Monimorillonite (Wyoming) SWy-1(SWy-2)
ORIGIN: Newcastle formation, (cretaceous)
County of Crook, State of Wyoming, USA
LOCATION: NE 1/4 SE 1/4 Sec.18, T 57 N, R 65 W; 8, Topographic map: Seeley(15'), The upper 63 of recently stripped area was removed to expose clean, green upper Newcastle, Collected from which samples was taken, Oct. 3, 1972.
CHEMICAL COMPOSITION (%): SiO$_2$: 62.9, Al$_2$O$_3$: 19.6, TiO$_2$: 0.090, Fe$_2$O$_3$:3.35, FeO: 0.32, MnO: 0.006, MgO: 3.05, CaO: 1.68, Na2O: 1.53, K2O: 0.53, F: 0.111, P$_2$O$_5$: 0.049, S: 0.05, Loss on heating: −550° C.: 1.59; 550-1000° C.: 4.47, CO$_2$: 1.33.
CATION EXCHANGE CAPACITY (CEC): 76.4 meq/100 g, principal exchange cations Na and Ca.
SURFACE AREA: N2 area: 31.82+/−0.22 m$^2$/g
THERMAL ANALYSIS: DTA: endotherms at 185° C. (shoulder at 235° C.), desorption of water: 755° C., dehydroxylation; shoulder at 810° C., exotherms at 980° C. TG: Loss in dehydroxylation range: 5.53% (theory: 5%).
INFRARED SPECTROSCOPY: Typical spectrum for Wyoming bentonite with a moderateFe+3 content (band at 885 cm$^{-1}$). Quartz is detectable (band at 780, 800, 698, 400, and 373 cm$^{-1}$), a trace of carbonate (band at 1425 cm$^{-1}$).
STRUCTURE: (Ca·12 Na·32 K·05)[A13.01 Fe(III)·41 Mn·01 Mg·54Ti·02][Si7.98 Al·02]O20(OH)4, Octahedral charge: −0.53, Tetrahedral charge: −0.02, Interlayer charge: −0.55, Unbalanced charge: 0.05.

Stock solutions of pFI-1, SWy-3, and a mixture of pFI-1 and Swy-3 (25:75) were prepared by adding 20 mg of each clay nanoparticles to 10 ml phosphate buffered saline (PBS) (2 mg/ml in PBS). Each stock solution was further diluted in Dulbecco's modified Eagle's medium (DMEM) (Lonza, Walkersville, Md.) to create a 0.1 mg/ml working solution.

Cell Culture. Human malignant melanoma cell line SK-Mel-28, a skin primary melanoma from American Type Culture Collection (ATCC, Manassas, Va.), were grown in DMEM supplemented with 5% Fetal Bovine Serum (FBS) (HyClone Inc.) and antibiotic-antimycotic mix of 100 mg/ml penicillin, 100 mg/ml streptomycin, and 0.25 mg/ml amphotericin B (Mediatech, Manassas, Va.)(DMEM growth media). Cells were maintained in a Thermo culture incubator at 37° C. and 5% CO$_2$. The SK-MEL-28 cell line is available from the ATCC as ATCC HTB-72.

3-Day Dosage Response and Cell Proliferation and Viability Analyses. 4×10$^4$ SK-Mel-28 human melanoma cells were plated in each well of a 24-well tissue culture plate (Corning Inc.) and incubated in DMEM growth media overnight at 37° C. under 5% CO$_2$. Cells were divided into four groups then treated with a control media or treatment media at final concentrations of 2 µg/ml, 5 µg/ml, and 10 µg/ml of respective clay suspensions in DMEM growth media.

On day 3 after treatment, cells were washed with PBS, treated with 0.05% trypsin/0.53 mM EDTA solution for 2 minutes and detached from the dish. Viable cells and total cells were counted under phase-contrast microscope using a dye-exclusion hemocytometer technique. Cell viability was calculated by dividing the number of viable cells by the number of total cells (viable cells and non-viable cells). The results were recorded and graphed as a function of treatment clay concentration versus mean viable cells or cell viability. All treatments were performed in triplicate.

5-Day Timing Course of Cell Proliferation and Viability Assays. $8 \times 10^4$ SK-Mel-28 human melanoma cells were plated in each well of a 12-well tissue culture plate. The cells were incubated overnight in DMEM growth media at 37° C. and 5% $CO_2$. Cells were divided into four groups then treated with the 10 μg/ml of pFI-1, SWy-3, and mix of pFI-1 and SWy-3 (25:75), respectively, or with control media with no clay.

On days 1, 3, and 5 after treatment, melanoma cells were detached and counted using the dye-exclusion hemocytometer technique. The numbers of viable cells were calculated. Cell proliferation and cell viability were calculated by dividing the number of viable cells by the number of total cells. The results were recorded and graphed as a function of time versus mean number of viable cells or cell viability. All treatments were performed in triplicate.

Statistical Analysis. The GraphPad Prism 8 program was used for statistical analysis. A one-way analysis of variance (ANOVA) was used to identify a difference followed by Student T-tests. P-values less than 0.05 were considered statistically significant.

Cell viability and proliferation—3 day course. Nanoclay treatments reduced cell proliferation and cell viability in a dosage dependent manner in 3-day dosage response assay. Three days after treatment, the control group of melanoma cells exhibited the greatest number of cells and cell viability (100%), while the viable cells and cell viability in all treatment groups were greatly decreased (Table 1, FIGS. 1 and 2).

Figure 1:
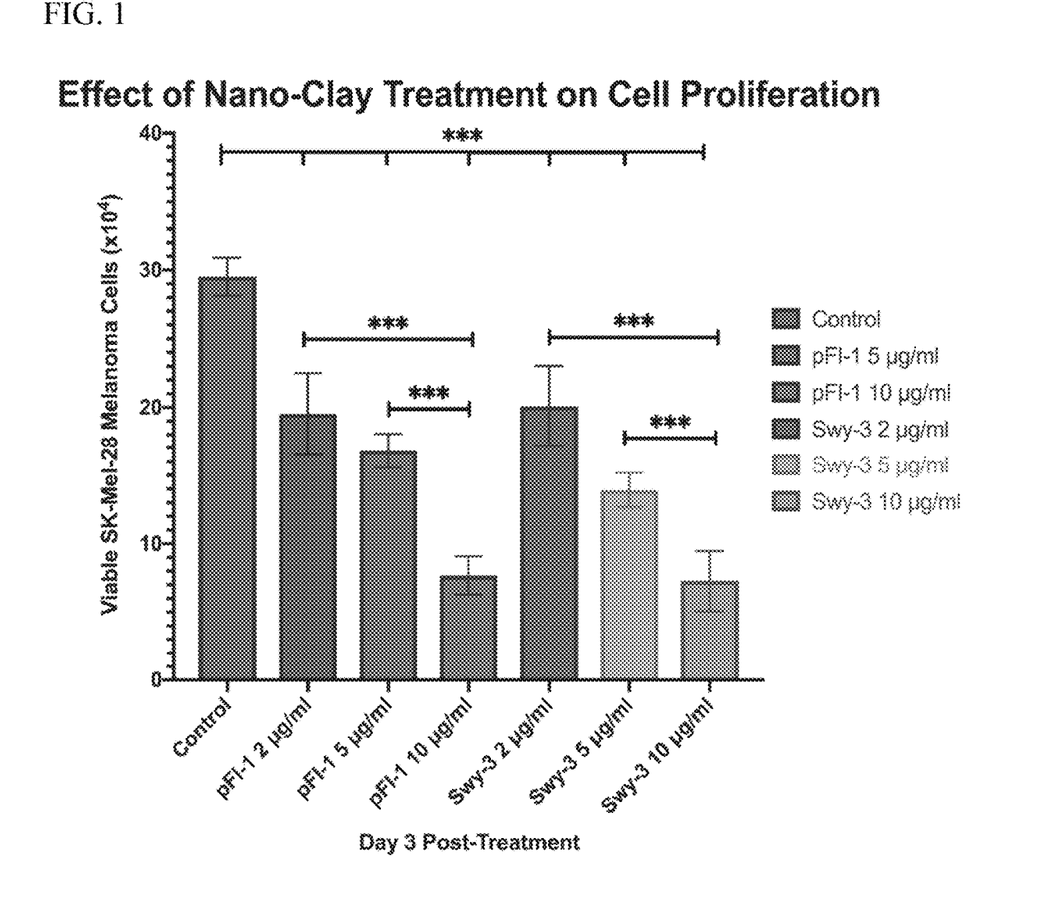
FIG. 1. Effect of nanoclay treatment on cell proliferation as determined on Day 3 of post-treatment. Nanoclay treatments reduced viable melanoma cells in a dosage dependent manner. SK-Mel-28 melanoma cells were treated for 3 days with pFI-1 and Swy-3 at concentrations of 2, 5 and 10 μg/ml, respectively. The mean viable cells for each treatment were counted and shown as columns. Standard deviation is represented in the figure by a bar attached to each column. Significant differences at $p<0.001$ are denoted by ***.

Viable melanoma cell numbers were greatly decreased in a dosage dependent manner when the concentrations of the treatment of both pFI-1 and Swy-3 were increased from 2 μg/ml to 5 μg/ml, and 10 μg/ml (Table 1, FIG. 1). Similarly, the viability of melanoma cells decreased markedly in a dosage dependent manner as the treatment concentrations of both pFI-1 and Swy-3 increased (Table 1, FIG. 2).

Figure 2:
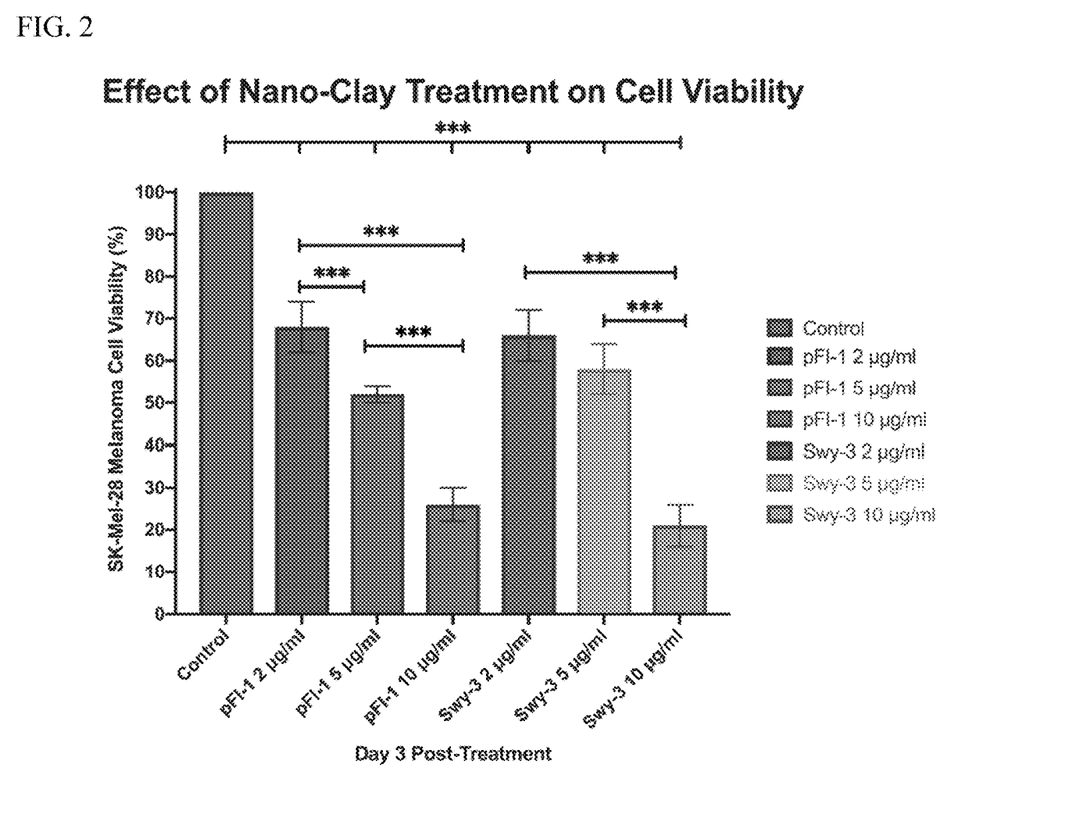
FIG. 2. Effect of nanoclay treatment on cell viability as determined on Day 3 of post-treatment. Nanoclay treatments reduced melanoma cell viability in a dosage dependent manner. SK-Mel-28 melanoma cells were treated for 3 days with pFI-1 and Swy-3 at concentrations of 2, 5 and 10 μg/ml, respectively. The numbers of viable cells and total cells were counted, and cell viability for each treatment was presented as columns. Standard deviation is represented in the figure by a bar attached to each column. Significant differences at $p<0.001$ are denoted by***, respectively.

The viability of melanoma cells treated with pFI-1 at concentrations of 2 μg/ml, 5 μg/ml, and 10 μg/ml were 68%, 52%, and 26%, respectively (Table 1, FIG. 2). This was a significant decrease compared to the control (all p<0.0001). Furthermore, cells treated with the 10 μg/ml concentration of pFI-1 resulted in the greatest decrease in viable cell count and cell viability (26%) amongst all pFI-1 treatment groups (Table 1, FIGS. 1 and 2; p<0.0001).

The viabilities of cells treated with S-3 at concentrations of 2 μg/ml, 5 μg/ml, and 10 μg/ml were 66%, 58%, and 21%, respectively (Table 1, FIG. 2). This was a significant decrease compared to the control (all p<0.0001). Furthermore, cells treated with 10 μg/ml of Swy-3 showed the greatest decrease in mean viable cells and viability (21%) amongst all Swy-3 treatment groups (Table 1, FIGS. 1 and 2; p<0.0001).

Cell viability and proliferation—5 day course. Nanoclay treatments reduced melanoma cell proliferation and viability over a 5-day timing course. Cell proliferation effects in a 5-day timing course with both nanoclay treatments at concentration of 10 μg/ml were evaluated. A 10 μg/ml concentration was chosen as it inhibited cell proliferation and viability the most in the 3 day assay described above.

Figure 3:
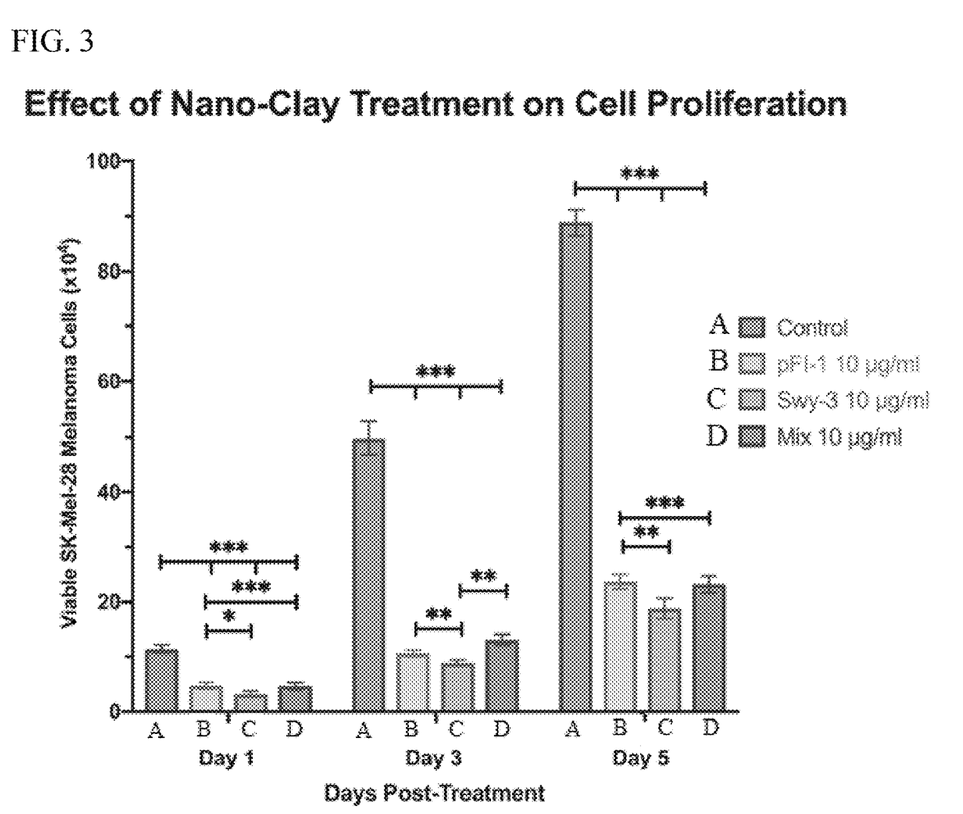
FIG. 3. Effect of nanoclay treatment on cell proliferation as determined on Days 1, 3 and 5. Nanoclay treatments inhibited melanoma cell proliferation during a 5-day timing course. SK-Mel-28 melanoma cells were treated with pFI-1, Swy-3 and the mix (25:75) at concentration of 10 μg/ml for 5 days. The numbers of viable cells and total cells were counted at days 1, 3 and 5 post-treatment, and cell viabilities for the treatments are shown. Standard deviation is represented in the figure by a bar attached to each column. Significant differences at $p<0.05$, $p<0.01$ and $p<0.001$ are denoted by *,  and *, respectively.
Figure 4:
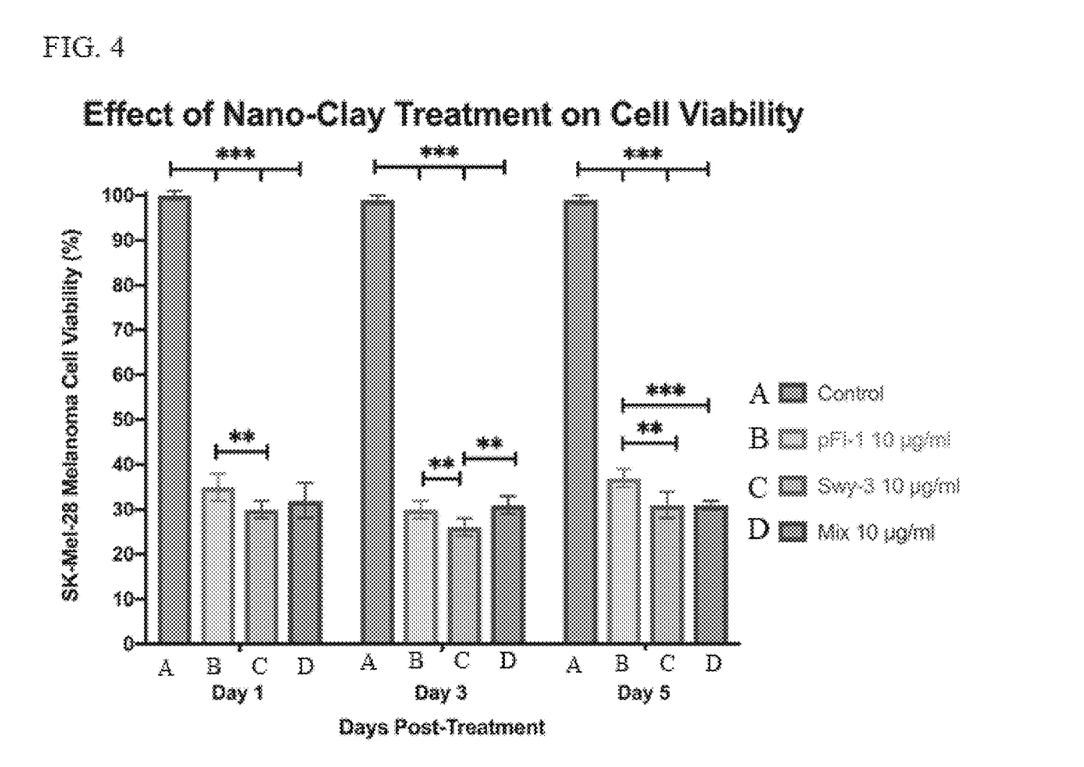
FIG. 4. Effect of nanoclay treatment on cell viability as determined on Days 1, 3 and 5. Nanoclay treatments reduced melanoma cell viability during a 5-day timing course. SK-Mel-28 melanoma cells were treated with pFI-1, Swy-3 and the mix (25:75) at concentration of 10 μg/ml for 5 days. The numbers of viable cells and total cells were counted at days 1, 3 and 5 post-treatment, and cell viabilities for the treatments are shown. Standard deviation is represented in the figure by a bar attached to each column. Significant differences at $p<0.01$ and $p<0.001$ are denoted by , and *, respectively.

There were significant decreases in mean viable cell counts and viabilities at all three timing points when comparing the 10 μg/ml concentration of pFI-1 treatment to the control. The viabilities of melanoma cells were 35%, 30% and 37% at days 1, 3 and 5, respectively, post-treatment (Table 2, FIGS. 3 and 4)(p<0.0001).

TABLE 1

The Effects of Nanoclay on Melanoma Cell proliferation and Viability - 3-day Dosage Response

| Treatment | Mean Viable Cells | Mean Viability (%) |
| --- | --- | --- |
| Control | 295200 | 100% |
| 2 μg/ml pFI-1 | 195200 | 68% |
| 5 μg/ml pFI-1 | 168000 | 52% |
| 10 μg/ml pFI-1 | 76800 | 26% |
| 2 μg/ml Swy-3 | 200800 | 66% |
| 5 μg/ml Swy-3 | 139200 | 58% |
| 10 μg/ml Swy-3 | 72800 | 21% |

Notes for Table 1.
Mean number of SK-Mel-28 melanoma cells and cell viability were determined for treatments at concentrations of 0 (control), 2, 5, and 10 μg/ml, respectively, 3 days post-treatment. The data demonstrated significant differences in viable cell counts and viability: 10 μg/ml pFI-1 vs control, p < 0.0001; 5 μg/ml pFI-1 vs control, p < 0.0001; 2 μg/ml pFI-1 vs control p < 0.0001; 10 μg/ml Swy-3 vs control, p < 0.0001; 5 μg/ml Swy-3 vs control, p < 0.0001; and 2 μg/ml Swy-3 vs control, p < 0.0001.

TABLE 2

The Effects of Nanoclay on Melanoma Cell Proliferation and Viability - 5-day Timing Course

| | Control | | 10 μg/ml pFI-1 | | 10 μg/ml Swy-3 | | 10 μg/ml Mix | |
| --- | --- | --- | --- | --- | --- | --- | --- | --- |
| Days | Viable Cells | Viability (%) | Viable Cells | Viability (%) | Viable Cells | Viability (%) | Viable Cells | Viability (%) |
| 1 | 114133 | 100% | 46933 | 35% | 32000 | 30% | 46333 | 32% |
| 3 | 497466 | 99% | 106400 | 30% | 88666 | 26% | 131250 | 31% |
| 5 | 888800 | 99% | 236866 | 37% | 188466 | 31% | 231916 | 31% |

Notes for Table 2.
Mean numbers of viable cells of SK-Mel-28 melanoma and cell viability for each treatment group, at 10 μg/ml, on days 1, 3, and 5 during a 5-day timing course are shown.

There were significant differences in mean viable cell counts between the control group and treatment groups across all three days (all p<0.0001). Furthermore, there were significant decreases in mean viable cell counts and viabilities at all three timing points when comparing the 10 µg/ml concentration of Swy-3 treatment to the control. The viabilities of melanoma cells were 30%, 26% and 31% at days 1, 3 and 5, respectively, post-treatment (Table 2, FIGS. 3 and 4) (p<0.0001). Lastly, there were significant decreases in mean viable cell counts and viabilities at all three timing points when comparing the 10 µg/ml concentration of mix of pFI-1 and Swy-3 (25:75) treatment to the control. The viabilities of melanoma cells were 32%, 31% and 31% at days 1, 3 and 5, respectively, post-treatment (Table 2, FIGS. 3 and 4; (p<0.0001).

The three-day dosage response analysis showed that both nanoclays, pFI-1 and SWy-3, led to a great decrease of viable melanoma cells. Proliferation of melanoma cells was decreased in a dosage dependent manner when the concentrations of the treatment of both nanoclay particles increased. Similarly, the viability of melanoma cells decreased markedly in a dosage dependent manner for both types of nanoclays.

In the Five-day timing course, with treatments of pFI-1, SWy-3 or their mix at concentration of 10 µg/ml, the results demonstrated that there were marked decreases in viable melanoma cells and cell viabilities with each treatment at all three timing points (days 1, 3 and 5). These data revealed that these nanoclays had strong inhibitory effects on melanoma cell proliferation and/or cell survival, showing its value for use for melanoma therapy.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 1.11, 2, 3, 3.75, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for reducing melanoma cell growth viability, comprising:
    mixing the melanoma cells with a treatment composition consisting essentially of at least one nanoclay selected from the group consisting of a palygorskite and a montmorillonite as an active ingredient, to form a cell growth mixture, then
    incubating the cell growth mixture for a time period in a range of from 3 to 5 days;
    wherein during the mixing the melanoma cells are present in a growth medium consisting essentially of water, amino acids, and glucose,
    wherein the treatment composition comprises the active ingredient in an amount in a range of from 2 to 25 µg/mL,
    wherein after the incubating, the melanoma cell growth viability of the melanoma cells is reduced by at least 50% in comparison to the melanoma cell growth viability of a control growth mixture that is mixed with a control composition that is the same as the treatment composition but does not comprise the active ingredient.

2. The method of claim 1, wherein the treatment composition comprises the active ingredient in a concentration in a range of from 2 to 20 µg of the per cc or per gram of the treatment composition.

3. The method of claim 1, wherein the treatment composition comprises the active ingredient in a concentration in a range of from 2 to 10 µg of the nanoclay per cc of per gram of the treatment composition.

4. The method of claim 1, wherein the at least one nanoclay consists essentially of the palygorskite.

5. The method of claim 1, wherein the at least one nanoclay consists of the palygorskite, having a formula $(Mg,Al)_2Si_4O_{10}(OH)\cdot 4H_2O$.

6. The method of claim 1, wherein the at least one nanoclay consists essentially of the montmorillonite.

7. The method of claim 1, wherein the at least one nanoclay comprises a Na-rich montmorillonite of a formula $(Na,Ca)_{0.33}(Al, Mg)_2(Si_4O_{10})$.

8. The method of claim 1, wherein the at least one nanoclay comprises a mixture of
    a palygorskite of a formula $(Mg,Al)_2Si_4O_{10}(OH)\cdot 4H_2O$ and
    a Na-rich montmorillonite of a formula $(Na, Ca)_{0.33}(Al, Mg)_2(Si_4O_{10})$.

9. The method of claim 1, wherein the treatment composition comprises no pigment and no dye.

10. The method of claim 1, wherein the at least one nanoclay consists essentially of the palygorskite and the montmorillonite.

11. The method of claim 1, wherein the at least one nanoclay consists of the palygorskite(s) and the montmorillonite(s).

12. The method of claim 1, wherein the at least one nanoclay consists of the palygorskite(s) and the montmorillonite.

13. The method of claim 1, wherein the at least one nanoclay consists of the montmorillonite(s).

14. The method of claim 1, wherein the melanoma cell growth viability of the melanoma cells is reduced by at least 63% in comparison to the melanoma cell growth viability of the control growth mixture that is mixed with the control composition that is the same as the treatment composition but does not comprise the active ingredient.

15. The method of claim 14, wherein the melanoma cell growth viability of the melanoma cells is reduced by at least 65%.

16. The method of claim 14, wherein the melanoma cell growth viability of the melanoma cells is reduced by at least 69%.

17. The method of claim 14, wherein the melanoma cell growth viability of the melanoma cells is reduced by at least 70%.

18. The method of claim 14, wherein the melanoma cell growth viability of the melanoma cells is reduced by at least 74%.

* * * * *